United States Patent [19]

Yaworsky et al.

[11] Patent Number: 5,430,935
[45] Date of Patent: Jul. 11, 1995

[54] METHOD FOR REPAIRING A COMBUSTION CHAMBER ASSEMBLY

[76] Inventors: Chester E. Yaworsky, 241 Wickham Rd., Glastonbury, Conn. 06033; Galen H. Reed, 58 Bigelow Rd., Colchester, Conn. 06415

[21] Appl. No.: 91,797
[22] Filed: Jul. 14, 1993
[51] Int. Cl.⁶ .................................... B23P 15/00
[52] U.S. Cl. .......................... 29/889.1; 29/402.03
[58] Field of Search ............. 29/889.1, 402.03, 402.04

[56] References Cited

U.S. PATENT DOCUMENTS

| | | |
|---|---|---|
| 4,451,979 | 6/1984 | Schuster ........................... 29/889.1 |
| 4,741,128 | 5/1988 | Reaves et al. ..................... 29/889.1 |
| 4,936,002 | 6/1990 | Silvestri, Jr. et al. ............. 29/889.1 |
| 5,205,465 | 4/1993 | Bogard et al. .................... 29/889.1 |
| 5,267,397 | 12/1993 | Wilcox ............................. 29/889.1 |

Primary Examiner—Irene Cuda

[57] ABSTRACT

A method of repairing a combustion chamber assembly 32 from an axial flow gas turbine engine 20 is disclosed. Various details are developed which facilitate repair of the combustion chamber assembly of the engine. In one detailed embodiment, a laser beam 80 separated the bulkhead of the combustion chamber assembly from the remainder of the assembly to allow independent repair of the bulkhead and the remainder of the assembly.

16 Claims, 4 Drawing Sheets

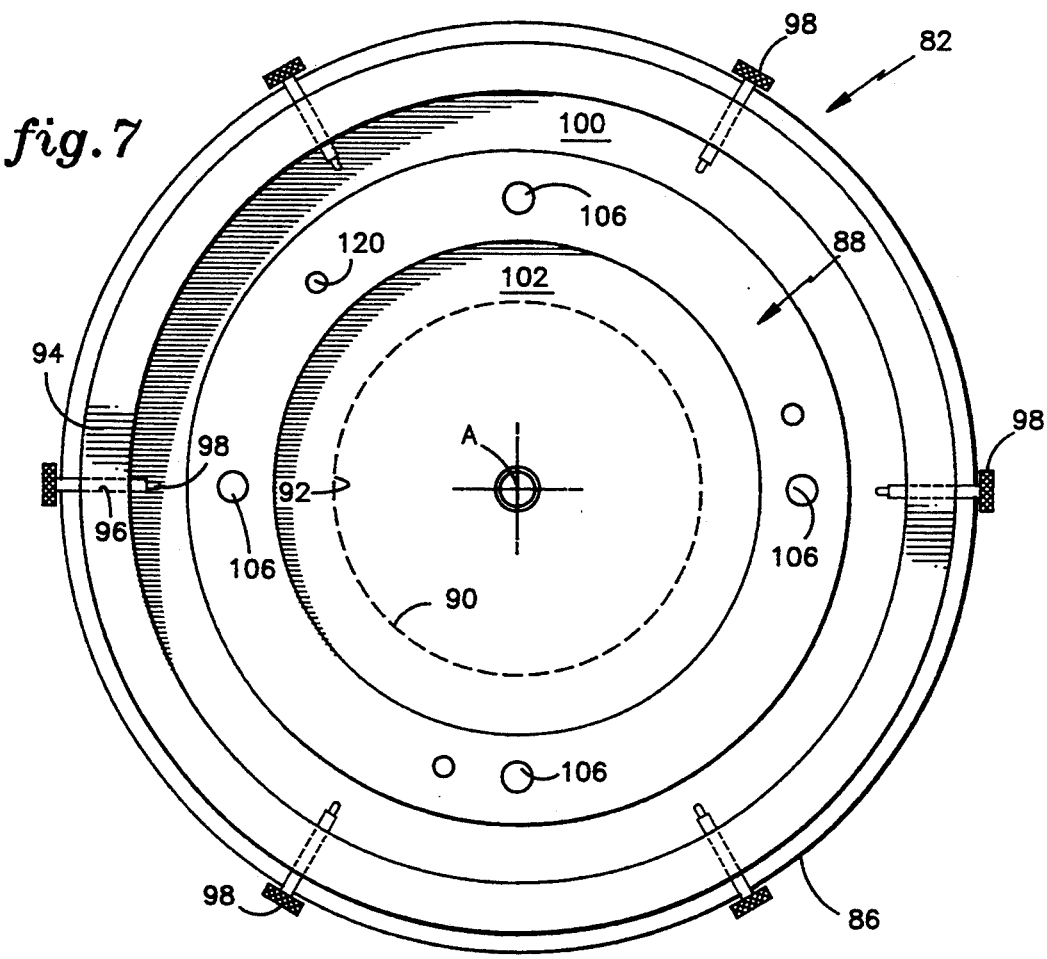
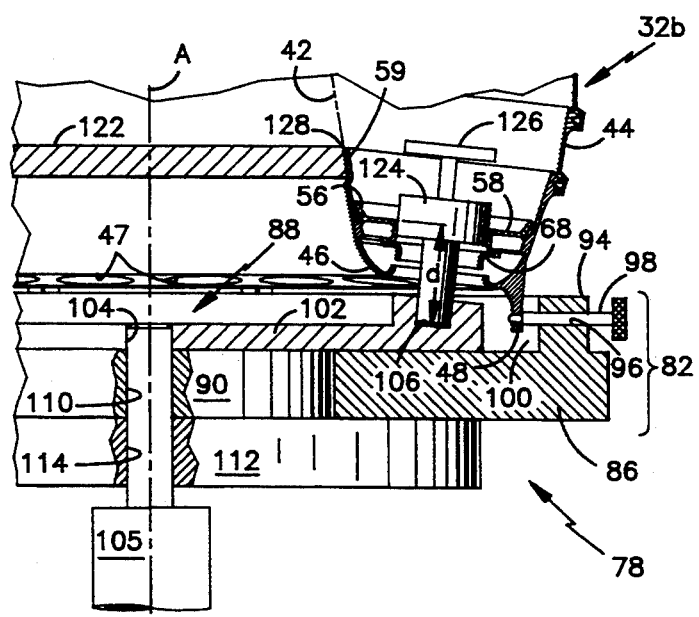

METHOD FOR REPAIRING A COMBUSTION CHAMBER ASSEMBLY

TECHNICAL FIELD

This invention relates to a gas turbine engine and more particularly to a method for repairing a combustion chamber assembly for such an engine. The present invention was developed for use in the field of axial flow gas turbine engines.

BACKGROUND

An axial flow gas turbine engine includes a compression section, a combustion section and a turbine section. The engine has a rotating rotor assembly. The rotor assembly includes a rotor disk-blade assembly which extends axially through the compression section, a rotor disk-blade assembly which extends axially through the turbine section, and a rotor shaft which extends axially connecting the rotor disk-blade assembly in the turbine section to the rotor disk-blade assembly in the compression section. A stationary stator assembly extends axially through the compression section and the turbine section of the engine. The stator assembly includes a case which circumscribes the rotor assemblies, supports which extend radially inwardly from the case for supporting the rotor assemblies, and stator vanes which extend radially inwardly from the case at a location upstream of each rotor assembly. The stator vanes prepare the gases for entry into the rotor disk-blade assembly.

A flow path for working medium gases extends axially through the sections of the engine. As the gases are flowed along the flow path, the gases are compressed in the compression section and burned with fuel in the pressurized combustion section to add energy to the gases. The gases flow to the turbine section where the rotor disk-blade assembly converts the energy in the gases into power to drive the compressor by turning the rotor shaft. The compressor and turbine sections have a special configuration, but only that of the combustion section is of interest here.

The combustion section includes a combustion chamber assembly extending circumferentially about an axis of symmetry. The combustion chamber assembly has an upstream end and a downstream end. The combustion chamber assembly includes an inner combustion chamber wall and an outer combustion chamber wall which extend between the ends. The walls are spaced radially leaving an annular combustion zone therebetween. A bulkhead assembly at the upstream end extends between the walls to join the walls together. The bulkhead assembly includes an inner ring, an outer ring and a bulkhead which extends between the two rings. The bulkhead is welded to the inner ring and outer ring to form an integral part.

The bulkhead has a first surface facing upstream and a second surface facing downstream. A dome-shaped hood for the combustion chamber extends over the upstream end of the combustion chamber assembly covering the first surface of the bulkhead. A plurality of lug mountings are an integral part of the hood and adapt the combustion chamber assembly for attachment in the engine. A plurality of openings are disposed circumferentially about the hood and the bulkhead. Each opening adapts the combustion chamber assembly to receive an associated fuel nozzle. Each fuel nozzle extends through the hood and the bulkhead for spraying fuel into the combustion chamber assembly.

A guide for each fuel nozzle is disposed in each opening in the bulkhead. The guides are spaced axially and spaced radially from the bulkhead leaving a passage for cooling air therebetween. A support, which is generally cylindrical in shape and extends upstream toward the combustion hood, is attached to the bulkhead and the guide to support the guide from the bulkhead. An anti-rotation element extends between each fuel nozzle and each support to restrain the fuel nozzle against rotation.

It is critical to the operative life of the engine that the angle of each fuel nozzle in relation to the lug mountings remains within predetermined limits. If the nozzle is positioned incorrectly, fuel may be sprayed onto the combustion chamber assembly walls, and the walls may be burned.

In addition, the original engine has a temperature profile in the circumferential direction and the radial direction for the gases entering the high pressure turbine. The temperature profile of the gases exiting the combustion section around the annular combustion chamber assembly must substantially match some predetermined temperature profile. Improper alignment of the fuel nozzles may cause the gases exiting the combustion section to have an altered temperature profile representing a temperature differential around the annulus, and/or the radius of the combustion chamber assembly. The gases exiting at a temperature profile substantially different than that of the original engine may excessively heat the rotor blades and the stator vanes in the turbine section causing the rotor blades and the stator vanes to oxidize and eventually fail.

Typically, a repaired combustion chamber assembly may have a substantial temperature differential in its profile. The temperature profile causes premature rotor blade and stator vane failure in the turbine section. There is a inverse relationship between the quality of the repair and the rate of premature failure. Thus, the proper maintenance and repair of the combustion chamber assembly is vital to the durability the combustion chamber assembly and the turbine, and ultimately the performance of the aircraft.

The combustion chamber assembly is typically repaired two to three times in its life. Repairs may be performed on the supports for the fuel nozzle guides, the anti-rotation elements which rest on the supports, the openings for the fuel nozzle guides on the bulkhead and the walls of the combustion chamber assembly. Accessing the walls for repair requires that the inner wall be removed. Because the elements and areas on the bulkhead needing repair are directly beneath the hood of the combustion chamber assembly, the industry practice is to remove the hood from the combustion chamber assembly to gain access to these damaged elements and areas.

Removing the hood is normally done by utilizing a cutting apparatus and a holding apparatus. The first step is to mark an inside cut-line around the perimeter of the inner wall of the hood and to mark an outside cut-line around the perimeter of the outer wall of the hood. The next step is to place the combustion chamber assembly with the hood facing upwardly into the center of the cutting apparatus. Then the combustion chamber assembly is held firmly in place by the holding apparatus, a hydraulic sizing cluster.

The sizing cluster fits into the combustion chamber assembly and holds the combustion chamber assembly on the inner diameter of the combustion chamber hood at a position lower than the inside cut-line. The set up of the sizing cluster is time consuming and difficult, because using the sizing cluster requires working with many small parts. Once, the combustion chamber assembly is secure the cutting apparatus is used.

The cutting apparatus includes a crank arm, a fixed arm, an annular track and a cutting wheel. A gear system converts the rotary motion of turning the crank arm into the circumferential motion of the fixed arm traveling along the track. The cutting wheel is mounted on the end of the fixed arm. The cutting wheel is powered by an air system.

The cutting wheel is positioned along the inside cut-line and rotated as many revolutions around the combustion chamber assembly as is necessary to separate the metal surfaces along the inside cut-line. The cutting wheel is then positioned along the outside cut-line and rotated until the metal surfaces separate.

Despite the existence of such methods of repairing the combustion chamber assemblies, scientists and engineers working under the direction of applicants' assignee, are searching for methods of repairing the combustion chamber assembly in a way that prevents excessive shop repair and reassembly time and maintains the original temperature profile for the high turbine inlet.

SUMMARY OF INVENTION

This invention is in part predicated on recognizing the standard method of repairing a combustion chamber assembly in the gas turbine industry causes several problems. First, when the combustion chamber assembly is repaired it may need repairs to the outer combustion chamber wall, the bulkhead and the inner combustion chamber wall of the combustion chamber assembly.

The inner combustion chamber wall is normally riveted and is easily removed from the combustion chamber assembly leaving a hooded bulkhead portion of the combustion chamber assembly, which includes the outer combustion chamber wall and the bulkhead. The industry standard method leaves the outer wall and the bulkhead as one part, the hooded bulkhead portion of the combustion chamber assembly. The repairs to the walls and the bulkhead require special tools and training, so one shop within each repair department handles work on the walls and another shop handles repairs on the bulkhead. Repairs to the hooded bulkhead portion of the combustion chamber assembly must be done first by the shop that works on the outer wall then by the shop that works on the bulkhead. The standard method leads to a repair time for the hooded bulkhead portion of the combustion chamber assembly which is the sum of the repair times for the outer wall and the bulkhead.

Second, the combustion chamber hood is rigidly attached to the inner ring and the outer ring of the bulkhead assembly. This attachment along with inwardly extending flanges along the hood and excess support material make the hood a reinforcing element to the bulkhead assembly. Once the hood is removed, the bulkhead assembly is no longer rigid and the bulkhead assembly moves to a new angle in relation to the lug mountings. Fuel nozzles extend through the bulkhead; therefore, altering the bulkhead angle alters the critical relationship the fuel nozzles have with the lug mountings.

As mentioned earlier, improper alignment of the fuel nozzles may alter the temperature profile of the gases exiting the combustion chamber assembly and entering the high pressure turbine. The gases exiting at a temperature profile substantially different than that of the original engine may excessively heat the downstream array of stator vanes and rotor blades in the turbine causing destruction of the rotor blades and stator vanes. Using the standard method, the appropriate shop must attempt to manually correct the nozzle angle in reassembly.

Next, the industry standard method, as mentioned in the Background Section, utilizes a cutting wheel. The cutting wheel causes a substantial gap at the cut-lines which is greater than or equal to sixty (60) thousandths of an inch in width. Reassembly requires tedious manual labor at a high cost due to the need to add filler material to the substantial gap, to blend smooth surfaces, to contour the hood and to perform excessive welding operations. Repairs performed utilizing the cutting wheel not only increase the reassembly time, but may also have graver consequences.

The excessive welding necessary after using the cutting wheel can lead to a large temperature differential on the annular combustion chamber assembly by disrupting the air flow in the combustion chamber assembly. When air flow is disrupted, the amount of cooling around the annular combustion chamber assembly varies and causes the temperature within the combustion chamber assembly to change. The temperature differential causes variations in the temperature profile for the high pressure turbine inlet that can lead to premature failure of the turbine rotor blades and stator vanes; therefore, repairing in the prior art fashion decreases engine durability and efficiency.

Lastly, integrated into the hood are a plurality of lug mountings, which are the datum for the combustion chamber assembly. This invention recognizes that shops that perform repairs with the prior art method of removing the hood will produce a combustion chamber assembly not having the same relationship to the engine as the original combustion chamber assembly.

According to the present invention, a method of repairing a combustion chamber assembly having an annular bulkhead and a combustion chamber hood (having integrated lug mountings extending from the hood), includes separating the annular bulkhead from the combustion chamber assembly, fixing the bulkhead as one part and fixing a remaining hooded portion of the combustion chamber assembly as a second part and then reattaching the bulkhead to the hooded portion of the combustion chamber assembly.

In accordance with one embodiment of the present invention, the bulkhead is separated to allow repairs of the bulkhead and the hooded portion of the combustion chamber assembly to proceed at the same time rather than in series.

According to the present invention, a method of repairing a hooded bulkhead portion of the combustion chamber assembly of a gas turbine engine includes the steps of supporting the hooded bulkhead portion of the combustion chamber assembly on a repair apparatus; separating the hooded bulkhead portion of the combustion chamber assembly into at least two separate parts—a bulkhead and a hooded portion of the combustion chamber assembly; fixing the bulkhead and the hooded portion of the combustion chamber assembly independently; reattaching the bulkhead to the hooded portion of the combustion chamber assembly.

A primary feature of the present invention is a method, which includes gaining access to the damaged areas on or near the bulkhead by separating the bulkhead from the combustion chamber assembly. A feature of one embodiment of the invention is separating the bulkhead utilizing a laser cutting system. Another feature is positioning the portions of the combustion chamber assembly and the bulkhead utilizing the repair apparatus.

A principal advantage of the present invention is the speed of repairing a combustion chamber assembly which results from removing the bulkhead by allowing processing of the bulkhead and the hooded portion of the combustion chamber assembly to proceed independently. Another advantage is the durability and efficiency of a gas turbine engine employing a repaired combustion chamber assembly, which results from avoiding hood removal and avoiding use of the cutting wheel, thus maintaining the original temperature profile for the high turbine inlet around the annulus of the combustion chamber assembly. Yet another advantage is the speed and ease of reassembly which results from removing the bulkhead, by avoiding difficult manual alignment of the fuel nozzle angles. Speed and ease of reassembly also results from removing material with the laser system by allowing hand and possibly automated welding operations, Andy avoiding substantial material loss, thus avoiding the need to fill a substantial gap and sand surfaces smooth. Still another advantage is allowing the repaired combustion chamber assembly to have the same relationship with the engine, which results from avoiding removal of the hood.

The foregoing features and advantages of the present invention will become more apparent in the light of the following detailed description of the best mode for carrying out the invention and in the accompanying drawing.

BRIEF DESCRIPTION OF THE DRAWING

FIG. 7 is a cross-sectional view taken along line 7—7 of FIG. 6 showing a support assembly as it appears during the repair operation and the relationship between some of the elements of the support assembly that were discussed in FIG. 6.

FIG. 8 is a side elevation view of the combustion chamber assembly as it appears during a procedure for reassembly of a bulkhead to a hooded portion of the combustion chamber assembly.

BEST MODE FOR CARRYING OUT THE INVENTION

Figure 1:
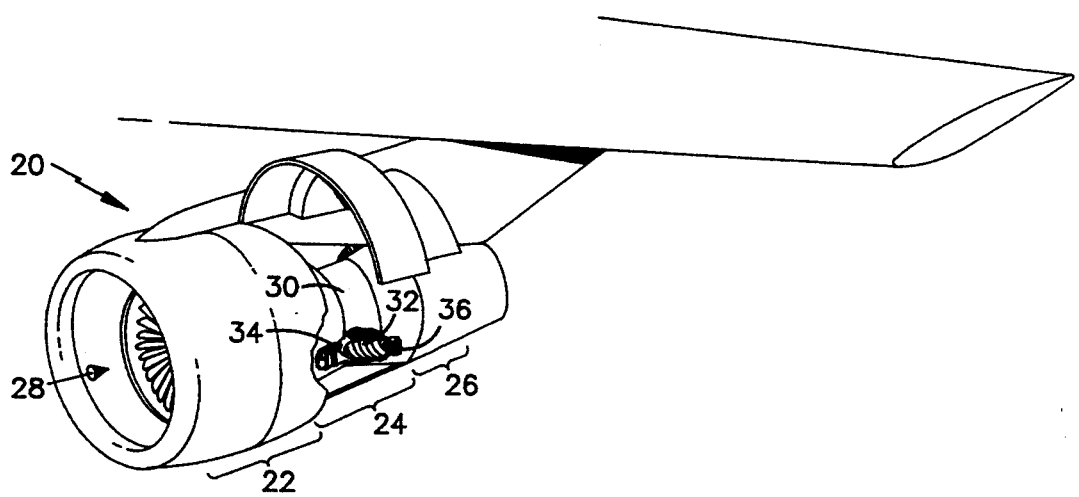
FIG. 1 is a perspective view of a gas turbine engine mounted on an aircraft wing broken away to show interior portions of a combustion section and a turbine section.

FIG. 1 is a perspective view of a gas turbine engine 20 mounted on an aircraft wing. The engine includes a compression section 22, a combustion section 24 and a turbine section 26. An annular flow path 28 for working medium gases extends axially through these sections of the engine. An engine case 30 extends axially through the engine to bound the flow path.

The engine case 30 is partially broken away to show a portion of the combustion section 24 and the turbine section 26. The combustion section includes a combustion chamber assembly 32 and a plurality of fuel nozzles, as represented by the single fuel nozzle 34. The turbine section includes an array of stator vanes, as represented by the stator vane 36. The vanes extend radially across the flow path for gases at a location downstream of the combustion chamber. An array of rotor blades (not shown) are downstream of the combustion chamber assembly and extend radially at a location downstream of the array of stator vanes.

Figure 2:
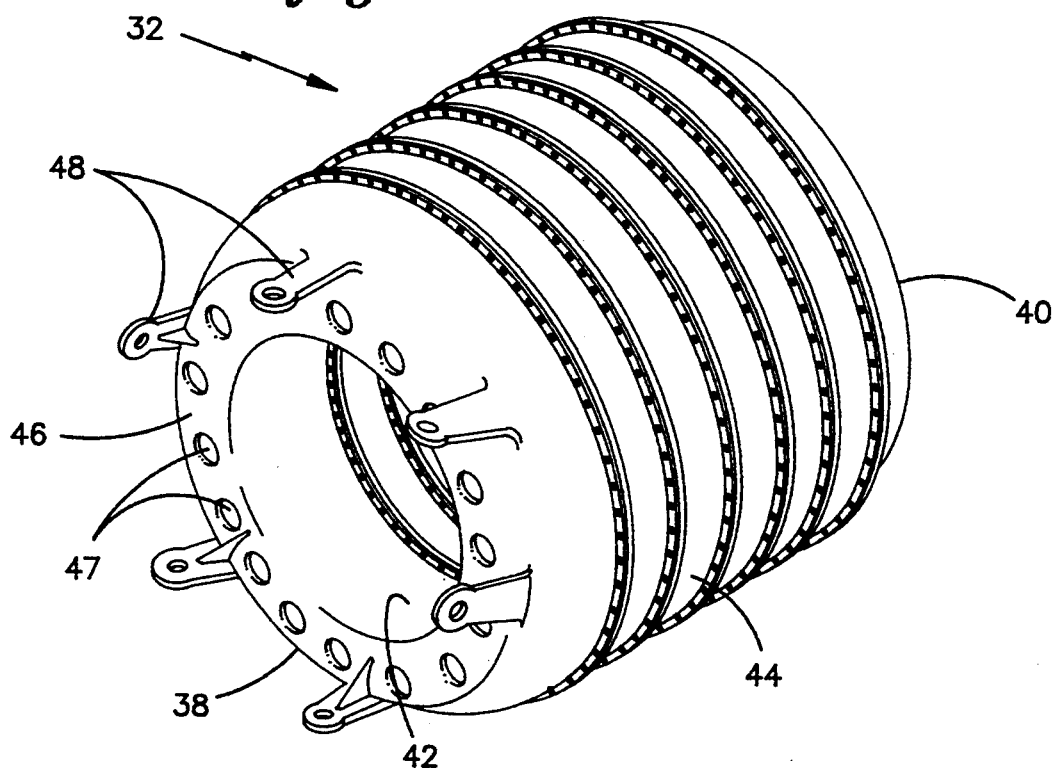
FIG. 2 is a perspective view in full of a combustion chamber assembly in an uninstalled condition.

FIG. 2 is a perspective view in full of the combustion chamber assembly 32 in an uninstalled condition. The combustion chamber assembly has an upstream end 38 and a downstream end 40. The combustion chamber assembly has an inner combustion chamber wall 42 and an outer combustion chamber wall 44 which extend between the ends. The walls are capped by a combustion chamber hood 46. A plurality of openings 47 are disposed circumferentially about the hood. A bulkhead assembly (not shown) extends between the walls and lies directly beneath the hood. A plurality of lug mountings 48 are an integral part of the hood.

Figure 3:
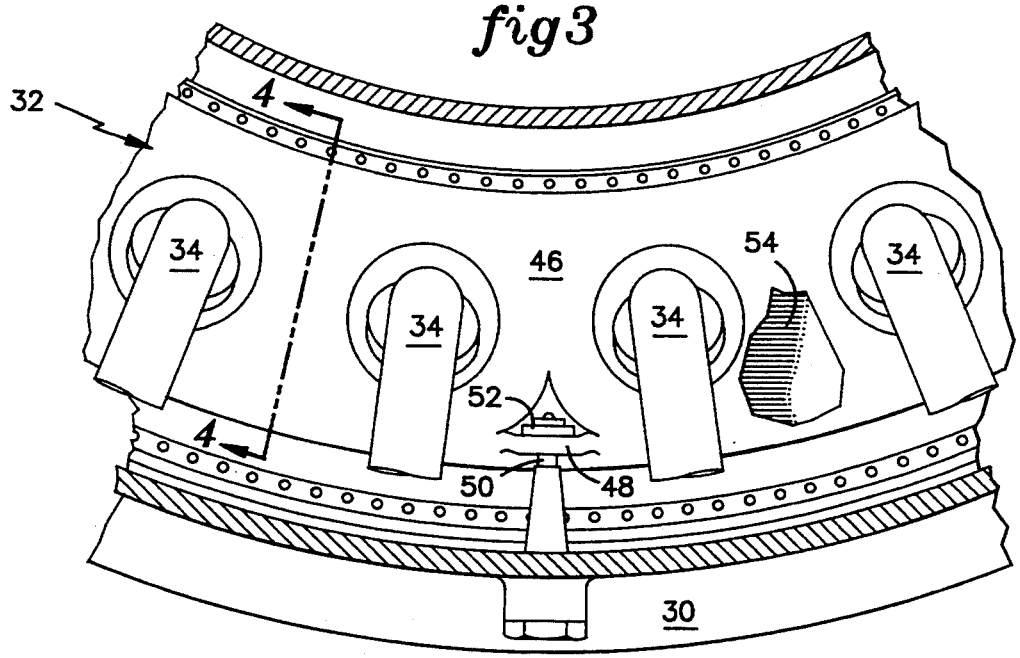
FIG. 3 is an end view of the combustion chamber assembly partially broken away to show a fuel nozzle and a combustion chamber hood with interior portions of a bulkhead shown.

FIG. 3 is an end view of the combustion chamber assembly 32. The combustion chamber assembly and the engine case 30 are partially broken away for clarity. The plurality of lug mountings, as represented by the lug mounting 48, extend from the combustion chamber assembly and each lug mounting is adapted to be attached to the engine case. In the embodiment shown, a pin 50 engages the case and the lug mounting and a bushing 52 protects the lug mounting from wear. The plurality of fuel nozzles 34 extend through the combustion chamber hood 46 and the bulkhead assembly 54 at a predetermined angle to spray fuel into the combustion chamber assembly.

Figure 4:
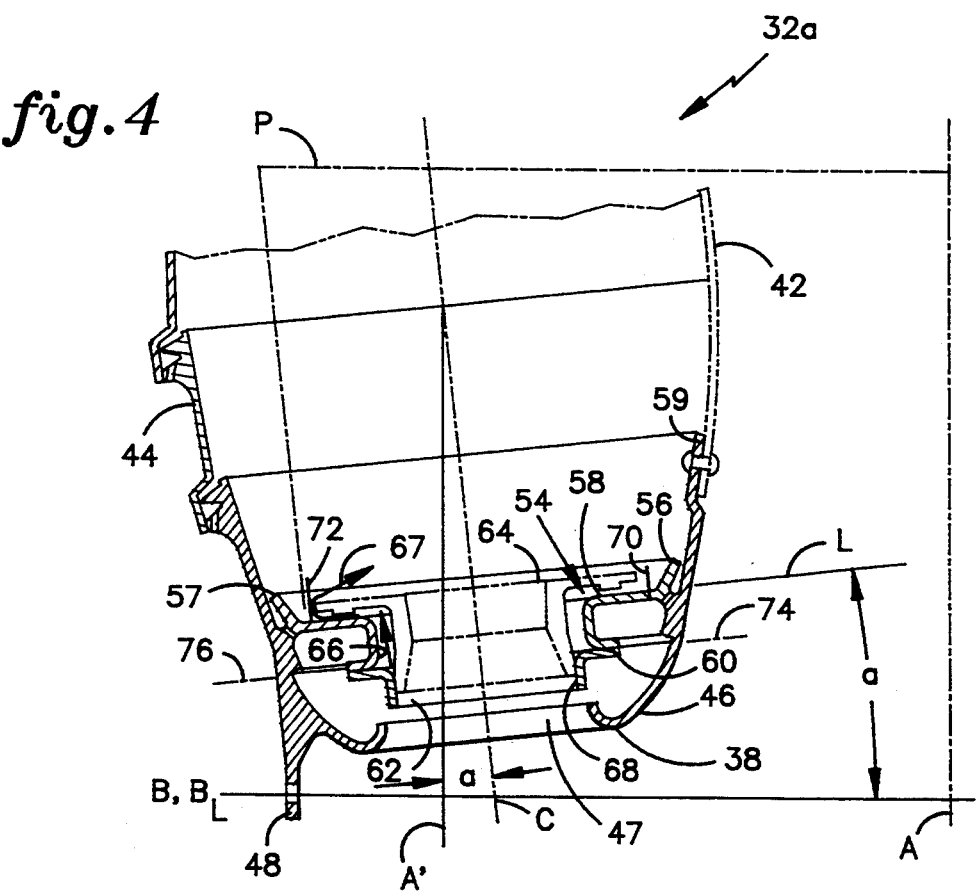
FIG. 4 is an enlarged side elevation view taken along the line 4—4 of the FIG. 3 showing the combustion chamber assembly as it appears during a repair operation after removal of an inner combustion chamber wall.

FIG. 4 is an enlarged side elevation view of a portion of the combustion chamber assembly 32a. The combustion chamber assembly has an axis of symmetry A. FIG. 4 shows the combustion chamber assembly as it appears during a repair operation after removal of the inner combustion chamber wall 42 (shown in phantom). Once the inner wall is removed, the remainder of the combustion chamber assembly forms the hooded bulkhead portion of the combustion chamber assembly 32a. The inner wall is integrally attached to the combustion chamber assembly, such as by rivets. The outer combustion chamber wall 44 is attached by welding.

The bulkhead assembly 54 extends between the two walls. The bulkhead assembly includes an inner ring 56, an outer ring 57 and a bulkhead 58 which extends between the two rings. The inner ring of the bulkhead assembly has an inner surface 59. The inner wall is riveted to the inner surface of the inner ring. The bulkhead has a first surface 60 which faces the upstream end 38 of the combustion chamber assembly. The combustion chamber hood 46 covers the first surface of the bulkhead. The plurality of lug mountings, as represented by the lug mounting 48, are an integral part of the hood.

The plurality of openings, as represented by the opening 47, are disposed circumferentially about the hood 46. A plurality of openings, as represented by the opening 62, are disposed circumferentially about the bulkhead. Each opening adapts the combustion chamber assembly to receive an associated fuel nozzle 34, which in this FIG. is broken away for clarity. Each fuel nozzle extends through the hood and the bulkhead for spraying fuel into the combustion chamber assembly.

A plurality of guides, as represented by the guide 64 (shown in phantom), are each disposed in each opening 62 in the bulkhead 58. The guides are spaced axially and spaced radially from the bulkhead leaving a passage for cooling air 66 therebetween. A flow path 67 for cooling air extends through the passage. A plurality of supports, as represented by the support 68, are attached to the first surface 60 of the bulkhead and the guide. The supports join the guides to the bulkhead. The supports extend toward the upstream end 38 of the combustion chamber assembly and the hood 46. The combustion chamber assembly may include other elements which are not shown, such as, a plurality of anti-rotation elements extending between each fuel nozzle and each support to restrain the fuel nozzle against rotation.

The combustion chamber assembly has a reference plane B which is defined by three points, where each of the three points is at the same relative location on a separate lug mounting 48. A centerline C for the opening 62 for the fuel nozzle shows the orientation of the fuel nozzle with respect to the reference plane B. A reference line A' is a line parallel to the axis of symmetry A and intersects the line C.

A radial reference plane P contains the axis A and the line C. The plane P intersects the bulkhead 58 at a reference line L. The plane P intersects the plane B at a reference line $B_L$.

An angle between the reference line L and the reference line $B_L$ is the angle of the bulkhead (bulkhead angle) with respect to the reference plane B for the combustion chamber assembly. It is also equal to an angle a between the line C and the line A'. Therefore, the bulkhead angle represents the angle of the bulkhead in relation to the lug mountings. The bulkhead angle a in the originally manufactured combustion chamber assembly is precisely determined and in the embodiment shown measures about fifteen degrees (15°).

An inner separation region 70 and an outer separation region 72 extend circumferentially about the bulkhead. The separation regions are commonly referred to as the cut-lines. In the prior art repair method an inside cut-line 74 and an outside cut-line 76 were used.

Figure 5:
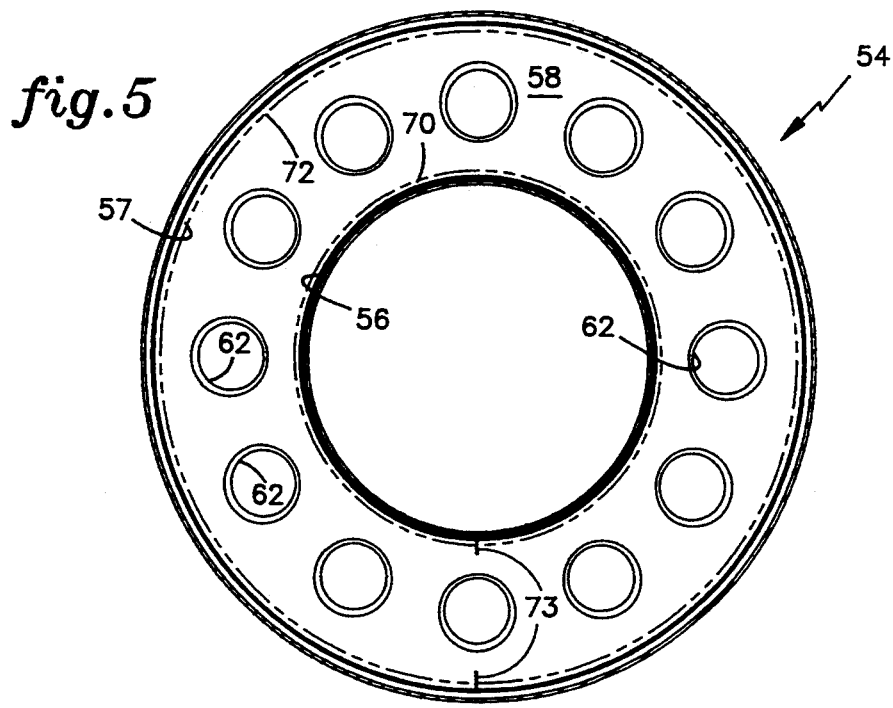
FIG. 5 is a cross-sectional view taken along the line 5—5 of FIG. 6 showing a cross-section of a bulkhead assembly.
Figure 6:
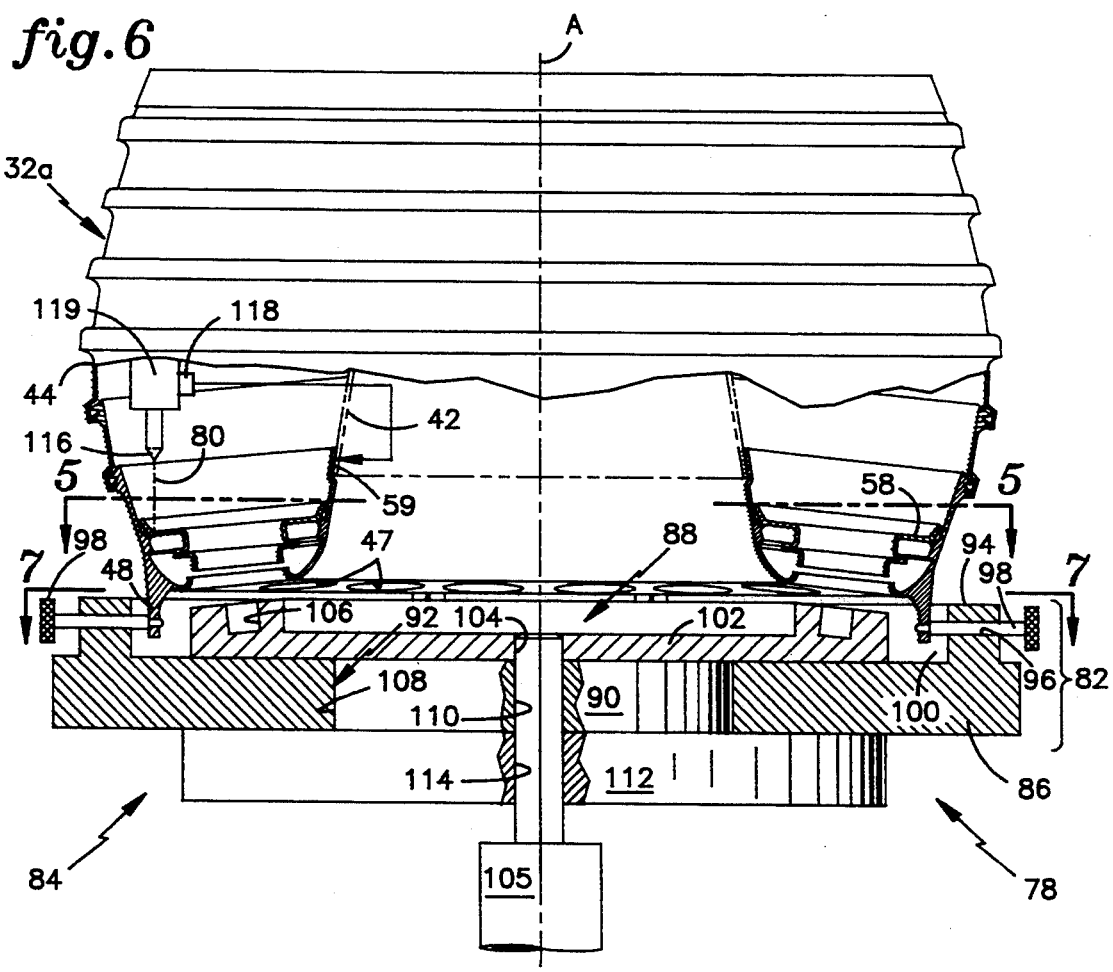
FIG. 6 is a side elevation view of a hooded bulkhead portion of the combustion chamber assembly with interior portions of the combustion chamber assembly broken away and shown as they appear during the repair operation.

FIG. 5 is a cross-sectional view of the bulkhead assembly 54 taken along line 5—5 of FIG. 6. The bulkhead assembly includes the inner ring 56 and the outer ring 57 joined by the bulkhead 58. The plurality of openings 62 for the fuel nozzles are disposed on the bulkhead. The bulkhead is separated along an inner circumference of the bulkhead at the cut-line 70, and along an outer circumference at the cut-line 72. Prior to separating the bulkhead, several reference lines 73 are drawn from the inner ring onto the bulkhead and the from the outer ring onto the bulkhead with a predetermined relationship to one another which assures the bulkhead is returned to the same circumferential position from which it was removed.

FIG. 6 is a side elevation view of the hooded bulkhead portion of the combustion chamber assembly 32a as it appears during a repair operation. A repair apparatus 78 for rotating and supporting the hooded bulkhead portion of the combustion chamber assembly engages the lug mountings 48 of the hooded bulkhead portion of the combustion chamber assembly. The repair operations occur about the axis of symmetry A of the combustion chamber assembly. A laser beam 80 is positioned within the combustion chamber assembly for cutting around the bulkhead 58.

The repair apparatus 78 includes a support assembly 82 and a rotator assembly 84. In the embodiment shown the support assembly includes a steel base plate 86, means for indexing the bulkhead 88 and an aluminum center plate member 90. In other embodiments, the support assembly may include the base plate and the means for indexing the bulkhead, where the center plate member has become an integral part of the base plate.

the base plate 86 includes a center opening 92 which adapts the base plate for rotation about the axis of symmetry A. The base plate has an outer rim 94 which extends upwardly from the base plate and circumferentially about the base plate. A plurality of pin holes, as represented by the pin hole 96, extend through the outer rim of the base plate. A plurality of locating pins, as represented by the locating pin 98, extend through the pin holes. A cavity 100 between the outer rim of the base plate and the means for indexing the bulkhead 88 receives the lug mountings (not shown). The lug mountings are engaged by the locating pins.

The means for indexing the bulkhead 88 includes an indexing plate 102 which attaches to the base plate 86. The indexing plate has a center hole 104 which adapts the plate for inserting of a locating cylinder 105 through the indexing plate. In other embodiments, the indexing plate is rigidly attached to the base plate, such as by bolts, and by virtue of this rigid attachment the indexing plate is centered on the rotator assembly. A plurality of plug holes as represented by the plug hole 106, shown by the dotted lines, are disposed around the circumference of the indexing plate. A plurality of plugs, shown in FIG. 8, engage the plug holes of the indexing plate.

The center plate member 90 includes locating surfaces 108 which engage the base plate 86 in the base plate center opening 92. The center plate member has a center hole 110 for receiving the locating cylinder 105.

The support assembly has bolt holes (not shown) for rigidly attaching the support assembly to the rotator assembly 84. The rotator assembly includes the means for causing the relative rotation of the support assembly with respect to the laser system 80, such as a turn table 112. The turn table has a center hole 114 for receiving the locating cylinder 105.

A cutting device, such as a laser beam 80, may be placed within the hooded bulkhead portion of the combustion chamber assembly 32a. The laser nozzle assembly 116 may be positioned near the bulkhead 58. The laser nozzle assembly includes a lens (not shown). A dial indicator 118 is disposed adjacent to the hooded bulkhead portion of the combustion chamber assembly. The dial indicator is connected to a fixed support, as represented by the dial indicator connected to a laser system 119 by a magnet. The dial indicator picks up on the inner surface 59 of the inner ring 56 of the bulkhead assembly FIG. 7 is a cross-sectional view taken along line 7—7 of FIG. 6 showing a support assembly 82 as it appears during a repair operation and the relationship between some of the elements of the support assembly that were discussed in FIG. 6. The support assembly holds the combustion chamber assembly 32 (not shown) in position. In the embodiment shown the support assembly includes the steel base plate 86, the means for indexing the bulkhead 88 and the center plate member 90.

The base plate 86 includes the center opening 92 which adapts the base plate for rotation about the axis of symmetry A of the combustion chamber assembly. The outer rim 94 extends upwardly from the base plate and circumferentially about the base plate. The pin holes 96 extend through the outer rim of the base plate. The locating pins 98 extend radially inwardly through the pin holes and have the relationship illustrated. The cavity 100 between the outer rim of the base plate and the means for indexing the bulkhead 88 receives the lug mountings 48. The lug mountings are engaged by the locating pins.

The means for indexing the bulkhead 88 includes the indexing plate 102 which attaches to the base plate 86. The plug holes 106 are disposed circumferentially about the indexing plate.

The base plate 86 and the indexing plate 102 of the support assembly each have a plurality of lifting holes 120 disposed circumferentially about the two plates. The base plate and the indexing plate of the support assembly have bolt holes (not shown) for rigidly attaching the support assembly to the rotator assembly (not shown).

The center plate member 90 engages the base plate 86 in the center opening 92 of the base plate.

The hole in the center of the support assembly extends through the center plate member 90 and the indexing plate 102 for receiving the locating cylinder (not shown).

FIG. 8 is a side elevation view of a combustion chamber assembly 32b. FIG. 8 shows the combustion chamber assembly as it appears during a procedure for reattaching the bulkhead 58 to the hooded portion of the combustion chamber assembly 32b. Once the inner wall 42 and the bulkhead are removed, the remainder of the combustion chamber assembly forms the hooded portion of the combustion chamber assembly. FIG. 8 also clarifies the features of some of the elements of the support assembly of the repair apparatus that were discussed in FIGS. 6,7.

The repair apparatus 78 supports the hooded portion of the combustion chamber assembly 32b. The repair apparatus includes the support assembly 82, the rotator assembly (not shown), the locating cylinder 105 and a bung plate 122. In the embodiment shown the support assembly includes the base plate 86, the means for indexing the bulkhead 88 and the center plate member 90.

As mentioned earlier, the means for indexing the bulkhead 88 has the plug holes 106 disposed around the circumference. Each plug hole has an angle parallel with the original bulkhead angle a, for orienting the bulkhead and a depth d for aligning the bulkhead with the surface adjacent to the inner ring 56 which remained attached to the combustion chamber assembly 32. The plugs 124 engage the plug holes for orienting and aligning the bulkhead in the reassembly of the combustion chamber assembly. Each plug has a hand knob 126 which extends outwardly from the plug to allow for the removal of the plug. Alternatively, any projection which allows for the removal of the plug would suffice.

The aluminum bung plate 122 has a surface 128 having a diameter which locates on the inner surface 59 of the inner ring 56 adjacent to the bulkhead 58 position. The bung has several holes (not shown) disposed around the circumference of the bung plate for a device for inserting and removing the bung plate from the combustion chamber assembly.

During operation of the gas turbine engine 20, shown in FIG. 1, gases are flowed along the flow path 28. As the gases are flowed along the flow path, the gases are compressed in the compression section 22 and burned with fuel in the pressurized combustion section 24 to add energy to the gases. The gases are flowed to the turbine section 26. The turbine section converts the energy in the gases into work and thrust.

The combustion section 24 includes the combustion chamber assembly 32. During the operation of the engine, the combustion chamber assembly is bathed in hot gases. These gases flowed through the combustion chamber assembly cause distress and cracking of parts of the combustion chamber assembly walls 42,44. The distress and cracking are due to forces exerted on the combustion chamber assembly and temperature cycles that accompany the operative conditions of the engine.

As shown in FIG. 4, The fuel nozzle guides 64 are each welded to an associated support 68. Cooling air is flowed along the flow path 67. The flow path for cooling air extends through a cooling air passage 66. The axial spacing through which the cooling passage extends decreases due to the forces and temperature cycles that occur during operation of the engine and the cooling air is subsequently cut off. As a result, the fuel nozzle guides must be replaced and any damage to the bulkhead must be repaired.

In addition, the movement of parts associated with the fuel nozzle 34, such as the anti-rotation elements, on the fuel nozzle guide support 68, during engine use causes wear on the anti-rotation element, such that the anti-rotation element may be replaced, and wear such that the support may be repaired. The present invention focuses on a method of repairing the combustion chamber assembly.

Typically, the combustion chamber assembly 32 will come to a repair department without the fuel nozzle guides 64 and the inner combustion chamber wall 42. If the fuel nozzle guides are present, they are machined off the bulkhead 58. If the inner wall 42 is in place, the rivets holding the inner wall are machined off and the inner wall is removed. The remainder of the combustion chamber assembly is referred to as the hooded bulkhead portion of the combustion chamber assembly 32a.

The present invention is a method for repairing the hooded bulkhead portion of the combustion chamber assembly 32a and includes the following steps. As shown in FIG. 6, the first step is to support the hooded bulkhead portion of the combustion chamber assembly on the repair apparatus 78. This step includes centering the center plate member 90 on the means for rotating the combustion chamber assembly, such as a turn table 112, by placing the center plate member on the turn table and extending the locating cylinder 105 through the center plate member and the hole 114 in the turn table.

Then, the base plate 86 with the means for indexing 88 attached is centered on the center plate member 90 by placing the base plate on the center plate member and extending the locating cylinder 105 through the indexing plate 102, the center plate member 90 and the turn table 112.

The next step is to center the hooded bulkhead portion of the combustion chamber assembly 32a on the support assembly 82. This includes the steps of engaging the lug mountings 48 with the locating pins 98 and adjusting the location of the hooded bulkhead portion of the combustion chamber assembly on the support assembly until it is concentric with the support assembly. The locating pins and the dial indicator 118 are utilized. The dial indicator is disposed adjacent to the hooded bulkhead portion of the combustion chamber assembly on a fixed support, such as the laser system 119, and runs on the inner surface 59 of the inner ring 56 of the bulkhead assembly The next step is to separate the hooded bulkhead portion of the combustion chamber assembly 32a into at least two separate elements, one of which is the bulkhead 58. Separating the bulkhead 58 includes the steps of causing two separations by making a separation cut on the bulkhead at an inner cut-line and an outer cut-line 72. Using a laser beam 80 results in a separation cut of between about six (6) thousandths of an inch in width to about eight (8) thousandths of an inch in width. Other embodiments may employ, for example, a water-jet having a separation cut of about thirty (30) thousandths to fourty (40) thousandths of an inch in width or a plasma cutting system having a separation cut of about sixteen (16) thousandths of an inch in width.

As shown in FIG. 5, the steps for causing the separation include marking the reference lines 73 on the bulkhead 58, the inner ring 56 and the outer ring 57 of the bulkhead assembly 54. As shown in FIG. 6, the laser beam 58 (Lumonics Corporation Laserdyne Model #780) is positioned for removing material along the inner separation area and the outer separation area on the bulkhead utilizing the cut-lines 70 and 72 respectively. The laser operates at a speed that is dependent on the material thickness of the bulkhead and a power setting that penetrates through the bulkhead material and avoids thermal distortions of adjacent surfaces or destructive exit damage to the hood 46. The laser is particularly adapted for this function.

The laser nozzle assembly 116 has a lens which focuses the energy from the laser beam so that the maximum energy discharge occurs at the bulkhead and the energy dissipates at locations beneath the bulkhead. Thus, after removing material through a rotation of three hundred and sixty (360) degrees along the inner separation area and the outer separation area the laser beam does not remove material from the hood or other structures. In addition the focal point of the laser beam coupled with the minimal heat discharged from the laser beam allows surfaces adjacent to the separation regions to experience minimal thermal distortions.

It is vital when utilizing the repair apparatus 78 which supports the combustion chamber assembly by the lug mountings 48 that during the cutting operation the transverse forces on the lug mountings are minimal and the resultant forces on the lug mountings put the lug mountings in compression. As discussed earlier, the lug mountings are weak in shear. Thus, the lug mountings may be unable to oppose the transverse forces of the cutting device and as a result the lug mountings may snap during a circumferential cutting operation. However, the laser beam imparts minimal transverse forces on the combustion chamber assembly during the circumferential cutting operation, so the lug mountings may not break.

In addition, the repair apparatus must hold the combustion chamber assembly securely during the cutting operation. Unlike the cutting wheel, the laser imparts minimal forces in the form of stress and vibration so the repair apparatus holds the combustion chamber securely. These forces do not make the combustion chamber assembly so unsteady on the repair apparatus that cutting is not possible.

Other embodiments of the present invention may utilize a variety of cutting devices other than the laser. One such device is the hand held air grinding apparatus with a cutting wheel. This is the conventional tool used to remove the hood in the prior art method and may be utilized here. Also, burrs may be utilized with the cutting wheel to improve this embodiment. Another device is a water-jet cutting system, with an abrasive agent in the water if necessary to cause the separation between cut surfaces. Some substance, such as foam, must be interposed between the jet and the hood in order to prevent the jet from causing destructive exit damage to the hood. Another possibility is a plasma cutting system that can be likened to a refined torch; however, some substance must be interposed between the plasma cutting system and the hood in order to prevent destructive exit damage to the hood. Another possibility is an electrical discharge machining device that utilizes an electrode to make the separations. Also, a lathe with a single point parting tool or a milling machine with a conventional milling cutter may be used. The term "cutting device," encompasses not only these embodiments, but includes any device which could make the cut without damaging the hood, the adjacent surfaces or the lug mountings while the repair apparatus is able to hold the combustion chamber assembly securely.

Once separating is complete, the next step is to repair the bulkhead 58 and the hooded portion of the combustion chamber assembly 32b independently. This step includes removing the bulkhead from the hooded bulkhead portion of the combustion chamber assembly 32a, removing the remaining hooded portion of the combustion chamber assembly from the repair apparatus 78, and repairing the bulkhead and the hooded portion of the combustion chamber assembly as necessary by the required specialists. Typically repair of these parts includes refurbishing any of the following the anti-rotation elements, the supports 68 for the fuel nozzle guides 64, the bulkhead 58 the outer wall 44 or any other item which requires repair.

As shown in FIG. 8, the last step is to reattach the bulkhead 58 to the hooded portion of the combustion chamber assembly 32b which includes the following steps. First, the hooded portion of the combustion chamber assembly is supported on the repair apparatus 78 by engaging the locating pins 98. The bulkhead 58 is positioned flush with the portion of the bulkhead surface on the hooded portion of the combustion chamber assembly utilizing the reference lines 73 and the plugs 124. The bung plate 122 is forcefully disposed inside the hooded portion of the combustion chamber assembly adjacent to the inner surface 59 of the inner ring 56 of the bulkhead assembly 54. The bung plate is located to maintain the circular shape of the inner diameter of the combustion chamber assembly 32 and the concentricity of the combustion chamber assembly during the repair operation. Copper chill plates are inserted in the openings 62 for the fuel nozzles 34. The next steps are tack welding along the inner circumference of the cut surface of the bulkhead then tack welding along the outer circumference of the cut surface of the bulkhead.

The order of many of the steps is not significant. One exception is the order of the tack welding steps. Each of the two cut surfaces of the bulkhead must be joined to a corresponding surface attached to the hooded portion of the combustion chamber assembly 32b. The inner circumference of the bulkhead is attached adjacent to the inner ring 56 and the outer circumference of the bulkhead is attached adjacent to the outer ring 57 of the bulkhead assembly 54. If welding of the outer circumference were to take place before welding of the inner circumference, the inner edge of the bulkhead would drop below the adjacent surface of the hooded portion of the combustion chamber assembly due to distortions of the bulkhead that accompany welding. Welding the inner circumference after welding the outer circumference would require a welder to simultaneously lift up the bulkhead, so the inner circumference is flush with the adjacent surface, and weld. Holding up the bulkhead and welding is difficult. When the inner circumference is welded first, the outer circumference distorts in a manner such that the outer edge of the bulkhead raises above the adjacent surface of the hooded portion of the combustion chamber assembly. Welding the outer circumference after welding the inner circumference would require the welder to simultaneously hold down the bulkhead, so the outer circumference is flush with the adjacent surface, and weld. Holding down the bulkhead and welding is relatively easy. Accordingly, tack welding should proceed from the inner circumference to the outer circumference.

The welding need not be completely finished at the inner circumference before proceeding to the outer circumference. Good results were obtained by providing a tack welds about one-quarter (0.25) of an inch to about one-half (0.50) of an inch apart around the inner circumference. Then providing tack welds about one-quarter (0.25) of an inch to about one-half (0.50) of an inch apart around the outer circumference. The following steps are to weld about four (4) inch to six (6) inch strips around the inner circumference at staggered locations and to weld the remainder of the inner circumference. Only the remainder of the inner circumference need be welded since the staggered weld strips are quality welds of the appropriate penetration. The remaining steps are to weld about four (4) inch to six (6) inch strips around the outer circumference at staggered locations and to weld the remainder of the outer circumference. Only the remainder of the outer circumference need be welded since the staggered weld strips are quality welds of the appropriate penetration. Although the plugs 124 allow the bulkhead angle a, as shown in FIG. 4, to be roughly correct welding distorts the angle somewhat. Because this angle is so critical to the life of the engine, the next step is to mechanically manipulate the combustion chamber assembly 32 to restore the original bulkhead angle a.

The step of manipulating the combustion chamber assembly 32 to restore the bulkhead angle a is an independent operation. The combustion chamber assembly is removed from the repair apparatus 78 and placed on a hydraulic cylinder and ram. A plate having a contour, such that the edges are chamfered and polished smooth so that the plate fits into the inner diameter of the combustion chamber assembly, is placed inside the combustion chamber assembly and pulled downward until the relationship between the bulkhead and the lug mountings, as represented by the bulkhead angle a, is restored.

The present invention has several advantages over the prior art method of repair. During the repair process the hooded bulkhead portion of the combustion chamber assembly 32a may need repairs to the outer combustion chamber wall 44 and the bulkhead 58. A principal advantage of the present invention is the speed of repairing the hooded bulkhead portion of the combustion chamber assembly which results from removing the bulkhead by allowing processing of the bulkhead as one part and processing of the outer wall as a second part. Each of these repairs which require special tools and training and a different shop within each repair department is able to handle work on either part at the same time. The industry standard method leaves the outer wall and bulkhead as one part, so repairs must be done first by the shop that works on the outer wall then by the shop that works on the bulkhead; therefore, it leads to a repair time that is the sum of the repair times for the bulkhead and the outer wall. Thus, with the present invention the repair time decreases from the sum repair times for each part to the time for the longest repair time between the bulkhead and the outer wall.

Another advantage is the durability and efficiency of a gas turbine engine 20 employing the repaired combustion chamber assembly 32, which results from avoiding hood 46 removal and utilizing the laser, thus maintaining the original temperature profile of the high turbine inlet around the annulus of the combustion chamber assembly. The hood is a reinforcing element to the bulkhead 58, which maintains the angle that the bulkhead makes in relation to the lug mountings 48, this angle is equal to the bulkhead angle a. By not removing the hood the present invention employs the hood to rigidly support the bulkhead and restrain the bulkhead from moving to a new angle. As shown in FIG. 3, the fuel nozzles 34 extend through the hood and the bulkhead; therefore, altering the bulkhead angle a, alters the fuel nozzle angle.

Recall, it is critical to the engine life that the angle of each fuel nozzle in relation to the bulkhead remains within predetermined limits, because misalignment can lead to damage of the combustion chamber assembly walls 42, 44 or the rotor blades or stator vanes 36 in the turbine section 26. An advantage of the present invention is that the bulkhead angle a and the fuel nozzle angle are unaltered by the process, thus by maintaining the original temperature profile for the high turbine inlet around the annulus of the combustion chamber assembly the efficiency of the engine is maintained.

Utilizing the laser beam 80 results in minimal material loss; therefore avoiding excessive welding operations. The excessive welding can lead to a large temperature differential on the combustion chamber annulus that causes premature failure of the rotor blades and stator vanes 36 in the turbine section 26. So, repairing by the present invention may not decrease the engine durability and efficiency.

Yet another advantage is allowing the repaired combustion chamber assembly 32 to have the same relationship with the engine as the original combustion chamber assembly which results from avoiding removal of the hood 46 and the lug mountings 48. Integrated into the hood are the lug mountings, which are the datum for the combustion chamber assembly. The present invention avoids removal of the hood and allows shops to perform repairs with the original reference points of the piece. Thus, the repaired combustion chamber assembly will have the same relationship with the engine as the original combustion chamber assembly.

Still another advantage is the speed and ease of reassembly which results from removing the bulkhead, by avoiding difficult manual alignment of the fuel nozzle angles and which results from removing material with a laser beam 80 by allowing hand and possibly automated welding operations, and by avoiding substantial material loss.

Although the invention has been shown and described with respect to detailed embodiments thereof, it should be understood by those skilled in the art that various changes in form and detail thereof may be made without departing from the spirit and the scope of the claimed invention.

We claim:

1. A method of repairing a hooded bulkhead portion of a combustion chamber assembly of the type having an upstream end, a downstream end, an axis of symmetry A, a bulkhead assembly which includes an inner ring, an outer ring spaced radially from the inner ring, and an annular bulkhead extending from the inner ring to the outer ring, the bulkhead having a number of openings for orienting fuel nozzles disposed circumferentially about the bulkhead, the combustion chamber assembly further including an outer wall extending downstream from the outer ring and a combustion chamber hood extending upstream from the outer ring, then radially inwardly then downstream to the inner ring, the combustion chamber hood having integrated lug mountings extending therefrom for supporting the combustion chamber assembly in the installed condition, comprising:
   (a) separating the annular bulkhead by removing a circumferentially extending portion of material on the bulkhead at a region between the openings for the fuel nozzles and the inner ring and by removing a circumferentially extending portion of material on the bulkhead at a region between the openings for the fuel nozzles and the outer ring; and
   (b) fixing the bulkhead as one part and a hooded portion of the combustion chamber assembly as a separate part;
   (c) reattaching the bulkhead to the hooded portion of the combustion chamber assembly;
   wherein removing the bulkhead from between the inner ring and the outer ring preserves the relationship the lug mountings have with the inner ring and the outer ring of the bulkhead assembly and,
   wherein leaving the combustion chamber hood undisturbed allows the combustion chamber hood to reinforce the inner ring and the outer ring and aids in maintaining the original orientation with respect to the lug mountings during the repair operation.

2. The method of repairing a hooded bulkhead portion of the combustion chamber assembly of claim 1, wherein the step of separating the bulkhead further includes the step of withdrawing the bulkhead without disturbing the position of the inner ring with respect to the lug mountings and without disturbing the position of the outer ring with respect to the lug mountings.

3. The method of repairing a hooded bulkhead portion of the combustion chamber assembly of claim 1, wherein the method employs a cutting device and a repair apparatus for supporting and positioning the combustion chamber assembly with respect to the cutting device the step of separating the bulkhead further includes the steps of:
   (a) positioning the combustion chamber assembly on the repair apparatus; and
   (b) causing relative rotation between the cutting device and the hooded bulkhead portion of the combustion chamber assembly.

4. The method of repairing a hooded bulkhead portion of the combustion chamber assembly of claim 3, wherein the step of causing relative rotation between the cutting device and the hooded bulkhead portion of the combustion chamber assembly takes place about an axis of rotation and further includes the step of maintaining the concentricity of the bulkhead with respect to an axis of rotation coinciding with the axis of symmetry of the hooded bulkhead portion of the combustion chamber assembly.

5. The method of repairing a hooded bulkhead portion of the combustion chamber assembly of claim 1, wherein the step of separating the annular bulkhead by removing a circumferentially extending portion of material on the bulkhead at a region between the openings for the fuel nozzles and the inner ring and by removing a circumferentially extending portion of material on the bulkhead at a region between the openings for the fuel nozzle guides and the outer ring further includes the step of removing less than about forty (40) thousandths of an inch in width of material at the separation regions.

6. The method of repairing a hooded bulkhead portion of the combustion chamber assembly of claim 5, wherein the step of removing less than about forty (40) thousandths of an inch in width of material at the separation regions further includes the step of positioning the hooded bulkhead portion of the combustion chamber assembly for passing the hooded bulkhead portion of the combustion chamber assembly through a laser beam.

7. The method of repairing a hooded bulkhead portion of the combustion chamber assembly of claim 1, wherein the step of separating the annular bulkhead by removing a circumferentially extending portion of material on the bulkhead at a region between the openings for the fuel nozzle guides and the inner ring and by removing a circumferentially extending portion of material on the bulkhead at a region between the openings for the fuel nozzle guides and the outer ring further includes the step of positioning the hooded bulkhead portion of the combustion chamber assembly with respect to a laser beam for passing the hooded bulkhead portion of the combustion chamber assembly through the laser beam.

8. The method of repairing a hooded bulkhead portion of the combustion chamber assembly of claim 1, wherein the step of separating the bulkhead further includes the steps of removing a circumferentially extending portion of material on the bulkhead at a region in close proximity to the inner ring and removing a circumferentially extending portion of material on the bulkhead at a region in close proximity to the outer ring.

9. The method of repairing a hooded bulkhead portion of the combustion chamber assembly of claim 8, wherein the steps of removing material at two circumferentially extending regions further includes the steps of removing a circumferentially extending portion of material on the bulkhead at a region coincident with the previous weld joint adjacent to the inner ring and by removing a circumferentially extending portion of material on the bulkhead at a region coincident with the previous weld joint adjacent to the outer ring.

10. The method of repairing a hooded bulkhead portion of the combustion chamber assembly of claim 1, wherein the step of fixing the bulkhead as one part and the hooded portion of the combustion chamber assembly as a separate part further includes the step of the restoring the bulkhead and the hooded portion of the combustion chamber assembly during time periods which partly coincide.

11. The method of repairing a hooded bulkhead portion of the combustion chamber assembly of claim 1, wherein the step of reattaching the bulkhead to the hooded portion of the combustion chamber assembly further includes the step of positioning the bulkhead with respect to the hooded portion of the combustion chamber assembly which further includes the steps of axially locating the bulkhead with respect to the inner ring and the outer ring and circumferentially locating the bulkhead with respect to the lug mountings.

12. The method of repairing a hooded bulkhead portion of the combustion chamber assembly of claim 11, wherein the step of positioning the bulkhead further includes the step of orienting the bulkhead so that the angle of the bulkhead with respect to the reference plane defined by the lug mountings is within predetermined limits established for a newly manufactured combustion chamber assembly.

13. The method of repairing a hooded bulkhead portion of the combustion chamber assembly of claim 1, wherein the step of reattaching the bulkhead to the hooded portion of the combustion chamber assembly further includes the step of disposing a bung plate within the hooded portion of the combustion chamber assembly to minimize the distortion the bulkhead experiences during reassembly and to maintain the concentricity of the inner ring of the bulkhead assembly.

14. A method for repairing a hooded bulkhead portion of a combustion chamber assembly of the type having an upstream end, a downstream end, an axis of symmetry, a bulkhead assembly at the upstream end which includes an inner ring and an outer ring spaced radially with an annular bulkhead extending between the two rings, the bulkhead having a number of openings for orienting fuel nozzles disposed circumferentially about the bulkhead, an outer wall extending from the outer ring downstream and a combustion chamber hood which extends upstream from the outer ring, then radially inwardly then downstream to connect with the inner ring, the combustion chamber hood having integrated lug mountings which extend upstream from the combustion chamber hood, comprising:

(a) supporting the hooded bulkhead portion of the combustion chamber assembly on a repair apparatus of the type having a support assembly having a base plate which adapts for receiving a center plate member, locating pins which extend radially, a means for indexing the bulkhead which rests on the base plate, the means for indexing the bulkhead including a indexing plate, a plurality of plug holes disposed circumferentially about the indexing plate, and a plurality of plugs which cooperate with the plug holes, and a center plate member on which the base plate rests, the support assembly adapts for attaching to a means for rotating the support assembly, which includes the steps of
  (1) centering the center plate member on the means for rotating,
  (2) centering the base plate with the means for indexing attached on the center plate member,
  (3) centering the hooded bulkhead portion of the combustion chamber assembly on the support assembly,;
(b) separating the hooded bulkhead portion of the combustion chamber assembly into at least two separate elements one of which is the bulkhead which includes the steps of
  (1) marking reference lines on the bulkhead, the inner ring and the outer ring of the bulkhead assembly,
  (2) removing a separation region between cut surfaces on the bulkhead at an outer separation area between about six (6) thousandths of an inch in width to about eight (8) thousandths of an inch in width,
    (i) positioning a laser beam for cutting along the outer separation area on the bulkhead of the hooded bulkhead portion of the combustion chamber assembly,
    (ii) operating the laser beam at a speed that is dependent on the material thickness of the bulkhead and a power setting that will penetrate through the bulkhead material and avoid thermal distortions of adjacent surfaces or destructive exiting damage, and
    (iii) cutting three hundred and sixty (360) degrees along the outer separation area,
  (3) removing a separation region between cut surfaces on the bulkhead at an inner separation area between about six (6) thousandths of an inch in width and about eight (8) thousandths of an inch in width,
    (i) positioning the laser beam for cutting along the inner separation area on the bulkhead of the hooded bulkhead portion of the combustion chamber assembly,
    (ii) operating the laser beam at a speed that is dependent on the material thickness of the bulkhead and a power setting that will penetrate through the bulkhead material and avoid thermal distortions of adjacent surfaces or destructive exiting damage, and
    (iii) cutting three hundred and sixty (360) degrees along the inner separation area;
(c) fixing the bulkhead and a hooded portion of the combustion chamber assembly wherein repairs to the bulkhead and the hooded portion of the combustion chamber assembly proceed independently, including the steps of
  (1) detaching the bulkhead from the hooded bulkhead portion of the combustion chamber assembly,
  (2) removing the hooded portion of the combustion chamber assembly from the repair apparatus, and
  (3) repairing the bulkhead and the hooded portion of the combustion chamber assembly;
(d) reattaching the bulkhead to the hooded portion of the combustion chamber assembly, which includes the steps of
  (1) supporting the hooded portion of the combustion chamber assembly on the repair apparatus by engaging the locating pins,
  (2) positioning the bulkhead flush with the inner portion of bulkhead surface on the hooded portion of the combustion chamber assembly using the reference lines and plugs, (3) disposing a bung plate into the center of the hooded portion of the combustion chamber assembly adjacent to the inner ring which includes the step of forcing the bung plate into the hooded portion of the combustion chamber assembly, (4) inserting copper chill plates in the openings for the fuel nozzles, (5) first, welding along the inner circumference of the bulkhead, (6) then, welding along the outer circumference of the bulkhead, (7) restoring the predetermined relationship between the bulkhead and the lug mountings.

15. A method for repairing a hooded bulkhead portion of a combustion chamber assembly of the type having an upstream end, a downstream end, an axis of symmetry, a bulkhead assembly at the upstream end which includes an inner ring and an outer ring spaced radially with an annular bulkhead extending between the two rings, the bulkhead having a number of openings for orienting fuel nozzles disposed circumferentially about the bulkhead, an outer wall extending from the outer ring downstream and a combustion chamber hood which extends upstream from the outer ring, then radially inwardly then downstream to connect with the inner ring, the combustion chamber hood having integrated lug mountings which extend upstream from the combustion chamber hood, comprising:

(a) supporting the hooded bulkhead portion of the combustion chamber assembly on a repair apparatus of the type having a support assembly having a base plate which adapts for receiving a center plate member, locating pins which extend radially, a means for indexing the bulkhead which rests on the base plate, the means for indexing the bulkhead including a indexing plate, a plurality of plug holes disposed circumferentially about the indexing plate, and a plurality of plugs which cooperate with the plug holes, and a center plate member on which the base plate rests, the support assembly adapts for attaching to a means for rotating the support assembly and having a center hole which adapts for receiving a locating cylinder, which includes the steps of (1) centering the center plate member on the means for rotating, which includes the steps of
   (i) placing the center plate member on the means for rotating, and
   (ii) extending the locating cylinder through the center plate member and the hole in the means for rotating, (2) centering the base plate with the means for indexing attached on the center plate member, which includes the steps of
   (i) placing the base plate with the means for indexing attached on the center plate member, and
   (ii) extending the locating cylinder through the means for indexing and the center plate member, (3) centering the hooded bulkhead portion of the combustion chamber assembly on the support assembly, which includes the steps of
   (i) engaging the plurality of lug mountings with the plurality of locating pins, and
   (ii) adjusting the location of the hooded bulkhead portion of the combustion chamber assembly on the support apparatus utilizing the locating pins and a dial indicator until concentricity of the hooded bulkhead portion of the combustion chamber assembly is achieved;

(b) separating the hooded bulkhead portion of the combustion chamber assembly into at least two separate elements one of which is the bulkhead which includes the steps of (1) marking reference lines on the bulkhead, the inner ring and the outer ring of the bulkhead assembly, (2) removing a separation region between cut surfaces on the bulkhead at an outer separation area between about six (6) thousandths of an inch in width to about eight (8) thousandths of an inch in width,
   (i) positioning a laser for cutting along the outer separation area on the bulkhead of the hooded bulkhead portion of the combustion chamber assembly,
   (ii) operating the laser at a speed that is dependent on the material thickness of the bulkhead and a power setting that will penetrate through the bulkhead material and avoid thermal distortions of adjacent surfaces or destructive exiting damage, and
   (iii) cutting three hundred and sixty (360) degrees along the outer separation area, (3) removing a separation region between cut surfaces on the bulkhead at an inner separation area between about six (6) thousandths of an inch in width and about eight (8) thousandths of an inch in width,
   (i) positioning the laser for cutting along the inner separation area on the bulkhead of the hooded bulkhead portion of the combustion chamber assembly,
   (ii) operating the laser at a speed that is dependent on the material thickness of the bulkhead and a power setting that will penetrate through the bulkhead material and avoid thermal distortions of adjacent surfaces or destructive exiting damage, and
   (iii) cutting three hundred and sixty (360) degrees along the inner separation area;

(c) fixing the bulkhead and a hooded portion of the combustion chamber assembly wherein repairs to the bulkhead and the hooded portion of the combustion chamber assembly proceed independently, including the steps of
   (1) detaching the bulkhead from the hooded bulkhead portion of the combustion chamber assembly,
   (2) removing the hooded portion of the combustion chamber assembly from the repair apparatus, and
   (3) repairing the bulkhead and the hooded portion of the combustion chamber assembly;

(d) reattaching the bulkhead to the hooded portion of the combustion chamber assembly, which includes the steps of
   (1) supporting the hooded portion of the combustion chamber assembly on the repair apparatus by engaging the locating pins,
   (2) positioning the bulkhead flush with the inner portion of bulkhead surface on the hooded portion of the combustion chamber assembly using the reference lines and plugs, (3) disposing a bung plate into the center of the hooded portion of the combustion chamber assembly adjacent to the inner ring which includes the step of forcing the bung plate into the hooded portion of the combustion chamber assembly, (4) inserting copper chill plates in the openings for the fuel nozzles, (5) first, tack welding along the inner circumference of the bulkhead, which includes the step of
   (i) tack welding at locations about one-quarter (0.25) of an inch to about one-half (0.50) of an inch apart around the inner circumference, (6) then, tack welding along the outer circumference of the bulkhead, which includes the step of
   (i) tack welding at locations about one-quarter (0.25) of an inch to about one-half (0.50) of an inch apart around the outer circumference, (7) then, welding along the inner circumference of the bulkhead, which includes the steps of
   (i) welding about four (4) inch to six (6) inch strips around the inner circumference at staggered locations, and
   (ii) then, welding the remainder of the inner circumference, (8) next, welding along the outer circumference of the bulkhead, which includes the steps of
   (i) welding about four (4) inch to six (6) inch strips around the outer circumference at staggered locations, and
   (ii) welding the remainder of the outer circumference, (9) restoring the predetermined relationship between the bulkhead and the lug mountings, which includes the steps of
   (i) removing the hooded bulkhead portion of the combustion chamber assembly from the repair apparatus,
   (ii) placing the hooded bulkhead portion of the combustion chamber assembly on a hydraulic cylinder and ram,
   (iii) placing a contoured plate inside the hooded bulkhead portion of the combustion chamber assembly, and
   (iv) pulling the plate downward until the predetermined relationship between the bulkhead and the lug mountings is restored.

16. The method of repairing a combustion chamber assembly of claim 1, wherein the combustion chamber assembly further includes an inner wall element spaced relatively in front of the outer wall chamber element and extending substantially parallel to the outer wall element, wherein the step of repairing the elements includes the step of separating the inner wall element.

* * * * *